(12) United States Patent
Zhang et al.

(10) Patent No.: US 8,506,939 B2
(45) Date of Patent: Aug. 13, 2013

(54) PERSONAL CARE COMPOSITION

(75) Inventors: Xiaodong Zhang, Livingston, NJ (US); Russell Lowell Kreeger, Fleminton, NJ (US); Tatiana Victorovna Drovetskaya, Basking Ridge, NJ (US)

(73) Assignee: Union Carbide Chemicals & Plastics Technology LLC

( * ) Notice: Subject to any disclaimer, the term of this patent is extended or adjusted under 35 U.S.C. 154(b) by 925 days.

(21) Appl. No.: 11/632,026

(22) PCT Filed: Jul. 22, 2005

(86) PCT No.: PCT/US2005/026115
§ 371 (c)(1),
(2), (4) Date: Jan. 9, 2007

(87) PCT Pub. No.: WO2006/023201
PCT Pub. Date: Mar. 2, 2006

(65) Prior Publication Data
US 2007/0253923 A1    Nov. 1, 2007

Related U.S. Application Data

(60) Provisional application No. 60/601,889, filed on Aug. 16, 2004.

(51) Int. Cl.
*A61K 8/73*      (2006.01)
*A61Q 19/00*    (2006.01)
*A61Q 19/10*    (2006.01)
*A61Q 5/00*      (2006.01)
*A61Q 5/02*      (2006.01)
*A61Q 5/12*      (2006.01)
*C08B 11/00*    (2006.01)

(52) U.S. Cl.
USPC ............................................. 424/70.1; 536/43

(58) Field of Classification Search
None
See application file for complete search history.

(56) References Cited

U.S. PATENT DOCUMENTS

| 3,472,840 A | 10/1969 | Stone et al. |
| 4,663,159 A | 5/1987 | Brode, II et al. |
| 6,156,297 A * | 12/2000 | Maurin et al. ............. 424/70.19 |

FOREIGN PATENT DOCUMENTS

| DE | 3301667 | 7/1984 |
| EP | 0556957 | 1/1993 |
| WO | WO 95/09599 | 4/1995 |
| WO | WO 01/48021 | * 7/2001 |
| WO | WO01048021 | * 7/2001 |

OTHER PUBLICATIONS

Dow, 2002. UCARE Polymers. AMERCHOL. pp. 1-23.*
Salamone,1996. Cellulosic ethers, cation. Polymeric Materials Encyclopedia, vol. 2:1113-1118.*

* cited by examiner

*Primary Examiner* — David J Blanchard
*Assistant Examiner* — Thurman Wheeler

(57) ABSTRACT

A personal care composition comprising a cationically modified cellulose ether, wherein the cellulose ether comprises from 0.5 to 4 moles of an ether substituent per mole of anhydroglucose repeat unit and the cellulose ether further substituted with a cationic substituent of the formula (I) wherein $R^1$, $R^2$ and $R^3$ each independently are $CH_3$ or $C_2H_5$, $R^4$ is $CH_2$—CHOH—$CH_2$ or $CH_2CH_2$, $A^{z-}$ is an anion, and z is 1, 2 or 3, and the cellulose ether comprises from 1.15 to 1.44 percent of cationic nitrogen, based on the total weight of the cellulose ether. The cationically modified cellulose ethers which comprise from 6,000 to 15,000 anhydroglucose repeat units are novel.

(I)

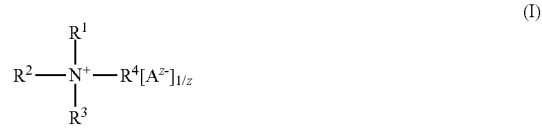

8 Claims, No Drawings

PERSONAL CARE COMPOSITION

CROSS-REFERENCE TO RELATED APPLICATION

This application is a 35 USC §371 national phase filing of PCT/US2005/026115, filed Jul. 22, 2005, which claims the benefit of U.S. Provisional Application No. 60/601,889, filed Aug. 16, 2004.

FIELD OF THE INVENTION

The present invention relates to personal care compositions comprising a cationically modified cellulose ether and to new cationically modified cellulose ethers.

BACKGROUND OF THE INVENTION

Cationically modified cellulose ethers and their use in personal care compositions have been known for many years.

U.S. Pat. No. 3,472,840 discloses quaternary nitrogen-containing cellulose ethers having a degree of polymerization (number of anhydroglucose repeat units) of 50 to 20,000, preferably 200 to 5,000, and their use as flocculents for paper pulp, coal dust, silica or clay or as a retention aid in the manufacture of paper.

The International Patent Publication WO 01/48021 discloses highly charged cationic cellulose ethers which are substituted with at least about 3.0 wt. % cationic substituent. These cellulose ethers are recommended for use in personal care applications, for example for enhanced substantivity to skin and hair.

Cellulose ethers which comprise 1.5-2.2 weight percent of cationic nitrogen are sold commercially by Amerchol under the trademark UCARE™ Polymers JR. Cellulose ethers which comprise 0.8-1.1 weight percent of cationic nitrogen are sold commercially by Amerchol under the trademark UCARE™ Polymers LR. These polymers have found wide use as water-soluble substantive conditioners for hair care and skin care products.

Although personal care compositions comprising a cationically modified cellulose ether have found wide acceptance, it would be still desirable to provide personal care compositions with improved properties.

Personal care compositions, such as hair care compositions and particularly skin care compositions, often comprise a moisturizing agent, such as sunflower seed oil. It is highly desirable that much of the moisturizing agent remains on the skin after it has been treated with the skin care or hair care composition and after the composition has rinsed off the skin. Therefore, one object of the present invention is to provide new personal care compositions which leave a high level of moisturizing agent, such as sunflower seed oil, on the skin after it has been treated with the personal care composition.

Furthermore, cationically modified cellulose ethers are widely used as conditioning agents, often in combination with insoluble active ingredients such as silicones, in hair care compositions. The conditioning properties of these products can be assessed by measuring the amount of work, which is required to comb through a hair tress treated with conditioning shampoo versus a control that does not comprise a conditioning agent. It is highly desirable to provide even greater reduction in wet combing work to enhance the consumer's positive usage experience when detangling and combing hair after shampooing. Therefore, another object of this invention is to provide new personal care compositions, such as hair care compositions, that deliver conditioning benefit, such as wet combing work reduction, to hair after it has been treated with the personal care composition.

Yet another object of the present invention is to provide new cationically modified cellulose ethers which are useful in such personal care compositions.

SUMMARY OF THE INVENTION

One aspect of the present invention is a personal care composition which comprises a cationically modified cellulose ether, wherein
the cellulose ether comprises from 0.5 to 4 moles of an ether substituent per mole of anhydroglucose repeat unit and
the cellulose ether is further substituted with a cationic substituent of the formula I

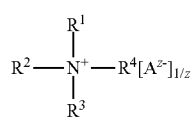

(I)

wherein
$R^1$, $R^2$ and $R^3$ each independently are $CH_3$ or $C_2H_5$,
$R^4$ is $CH_2$—CHOH—$CH_2$— or $CH_2CH_2$—,
$A^{z-}$ is an anion, and z is 1, 2 or 3, and
the cellulose ether comprises from 1.15 to 1.44 percent of cationic nitrogen, based on the total weight of the cellulose ether.

Another aspect of the present invention is the use of the above-mentioned cationically modified cellulose ether for preparing a personal care composition.

Yet another aspect of the present invention is a cationically modified cellulose ether, wherein
the cellulose ether comprises from 0.5 to 4 moles of an ether substituent per mole of anhydroglucose repeat unit,
the cellulose ether is further substituted with a cationic substituent of the formula I

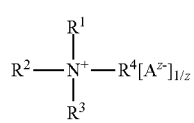

(I)

wherein
$R^1$, $R^2$ and $R^3$ each independently are $CH_3$ or $C_2H_5$,
$R^4$ is $CH_2$—CHOH—$CH_2$— or $CH_2CH_2$—,
$A^{z-}$ is an anion, and z is 1, 2 or 3, and
the cellulose ether comprises from 1.15 to 1.44 percent of cationic nitrogen, based on the total weight of the cellulose ether and from about 6,000 to about 15,000 anhydroglucose repeat units.

DETAILED DESCRIPTION OF THE INVENTION

The cationically modified cellulose ether comprises from 0.5 to 4, preferably from 1 to 3, more preferably from 1.5 to 2.5 moles of an ether substituent per mole of anhydroglucose repeat unit. The molar amount can be determined by the Morgan modification of the Zeisel method [P. W. Morgan, Ind. Eng. Chem., Anal. Ed., 18, 1500 (1946)]. It is understood by those skilled in the art that the ether substituent is different from the cationic substituent of formula I described below. Typical cellulose ethers include, for example, hydroxyethyl cellulose, hydroxypropyl cellulose, methyl cellulose, hydroxypropyl methyl cellulose, hydroxyethyl methyl cellulose or hydroxyethyl carboxylmethyl cellulose. If the cellulose ether comprises more than one type of ether substituents, their total molar number is within the ranges stated above. Preferred cellulose ethers include hydroxyethyl cellulose and hydroxypropyl cellulose. The most preferred cellulose ethers suitable for use in accordance with the present invention comprise hydroxyethyl groups. Preferably, these cellulose ethers have an M.S. (hydroxyethyl) of from 0.5 to 4, more preferably from 1 to 3, most preferably from 1.5 to 2.5. The M.S. (hydroxyethyl) designates the average number of moles of hydroxyethyl groups which have been attached by an ether linkage per mole of anhydroglucose repeat unit.

The cellulose ether is further substituted with a cationic substituent of the formula I

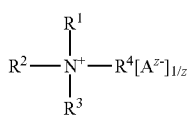
(I)

wherein
$R^1$, $R^2$ and $R^3$ each independently are $CH_3$ or $C_2H_5$,
$R^4$ is $CH_2$—CHOH—$CH_2$— or $CH_2CH_{2-5}$
$A^{z-}$ is an anion, and z is 1, 2 or 3.
Preferably, $R^1$ is methyl. More preferably, $R^1$, $R^2$ and $R^3$ are methyl. Preferably, $R^4$ is $CH_2$—CHOH—$CH_2$—. $A^{z-}$ is an anion with the valency of z, such as phosphate, nitrate, sulfate or halide. A halide, particularly chloride, is most preferred. Z is preferably 1 or 2, more preferably 1. The most preferred cationic substituents of the formula I are those wherein two or more, preferably each of $R^1$, $R^2$, $R^3$, $R^4$, $A^{z-}$ and z have the mentioned preferred meanings The cellulose ether comprises from 1.15 to 1.44 percent, preferably from 1.20 to 1.40 percent, of cationic nitrogen, based on the total weight of the cellulose ether. More than one particular cationic substituent of the formula I can be substituted onto the cellulose ether, but the total substitution level should be within the ranges set forth above. The percentage of cationic nitrogen is determined by analytical determination of the average weight percent of nitrogen per anhydroglucose repeat unit using an automated Buchi Kjeldahl distillation unit and titrating with an automated titrimeter.

Methods for preparing cationic substituents of the formula I, as well as methods for derivatizing cellulose ethers to contain such cationic substituents, are known to those skilled in the art, note for example WO 01/48021 A1.

Apart from the substituents disclosed above, the cellulose ether generally does not comprise another substituent, such as a hydrophobic alkyl or arylalkyl group having 8 to 24 carbon atoms.

The cationically modified cellulose ether is typically water-soluble. As used herein, the term "water-soluble" means that at least 1 gram, and preferably at least 2 grams of the cationically modified cellulose ether is soluble in 100 grams of distilled water at 25° C. and 1 atmosphere. The extent of water-solubility can be varied by adjusting the extent of ether substitution on the cellulose ether and the number of anhydroglucose repeat units. Techniques for varying the water solubility of cellulose ethers are known to those skilled in the art.

The viscosity of the cationically modified cellulose ether is generally from 100 to 10,000 mPa·s, preferably from 1,000 to 5,000 mPa·s, and most preferably from 2,000 to 3,000 mPa·s, measured as a 1.0 weight percent aqueous solution of the cellulose ether at 25° C. with a Brookfield viscosimeter.

Those cellulose ethers which have at least about 6,000, preferably at least about 7,000 anhydroglucose repeat units, and up to about 15,000, preferably up to about 12,000, more preferably up to about 10,000 anhydroglucose repeat units are novel compounds. The number of anhydroglucose repeat units are measured by Gel Permeation Chromatography using multiangle light scattering.

The cationically modified cellulose ether useful in the present invention can be produced by reacting a cellulose ether comprising from 0.5 to 4 moles of an ether substituent per mole of anhydroglucose repeat unit with a compound of formula II

(II)

wherein
$R^1$, $R^2$, $R^3$, $A^{z-}$ and z have the above-mentioned meanings and $R^5$ is

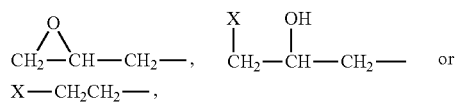

wherein X is halide, preferably bromide or chloride.

Quite surprisingly, it has been found that the above-described cationically modified cellulose ethers are more effective in personal care compositions than corresponding cationically modified cellulose ethers which comprise less than 1.15 or more than 1.44 percent of cationic nitrogen, based on the total weight of the cellulose ether. Specifically, the above-described cationically modified cellulose ethers are more effective in that they provide personal care compositions with an improved deposition of a moisturizing agent, such as sunflower seed oil on skin after the personal care composition, such as a skin care composition, has been rinsed off the skin. Furthermore, it has been unexpectedly found that the above-described cationically modified cellulose ethers also exhibit improved conditioning properties, such as greater reduction in wet combing work after hair has been shampooed with the personal care composition, such as a hair care composition, and rinsed with water. Surprisingly, it has also been found that cationically modified cellulose ethers comprising from 6,000 to 15,000, preferably from 6,000 to 12,000, more preferably from 7,000 to 10,000 anhydroglucose repeat units have an improved deposition of a moisturizing agent on skin than comparative cationically modified cellulose ethers comprising up to about 5,000 anhydroglucose repeat units.

Typical personal care applications include, for example, pharmaceutical and cosmetic compositions, such as contraceptive compositions, condom lubricants, vaginal ointments, ophthalmic compositions or skin creams. The more preferred end-use application for the above-described cationically modified cellulose ethers is as a component in hair or skin care compositions, such as shampoos, conditioners, cleansers, hand or body lotions, soaps, and body wash formulations. The most preferred end-use applications are skin cleansing or hair cleansing compositions.

The amount of the cationically modified cellulose ether present in the personal care composition will vary depending upon the particular composition. Typically, however, the personal care composition will comprise from about 0.05 to 5 weight percent, more preferably from about 0.1 to 1 weight percent of the cationically modified cellulose ether, based on the total weight of the personal care composition.

Typically the personal care composition also comprises one or more personal care ingredients, preferably water-insoluble active ingredients. A water-insoluble active ingredient generally has a water-solubility of less than 1 gram in 100 grams of distilled water at 25° C. and 1 atmosphere. Preferred water-insoluble active ingredients are (a) silicone oils and modifications thereof such as linear and cyclic polydimethylsiloxanes; amino, alkyl, alkylaryl, and aryl silicone oils; (b) fats and oils including natural fats and oils, preferably plant fats and oils, such as jojoba, soybean, sunflower, rice bran, avocado, almond, olive, sesame, persic, castor, coconut and mink oils; cacao fat; and animal fats and oils, such as beef tallow and lard; hardened oils obtained by hydrogenating the aforementioned oils; and synthetic mono, di and triglycerides such as myristic acid glyceride and 2-ethylhexanoic acid glyceride; (c) waxes such as carnauba, spermaceti, beeswax, lanolin, and derivatives thereof; (d) plant extracts; (e) hydrocarbons such as liquid paraffins, vaseline, microcrystalline wax, ceresin, squalene, pristan and mineral oil; (f) higher fatty acids such as lauric, myristic, palmitic, stearic, behenic, oleic, linoleic, linolenic, lanolic, isostearic, arachidonic and polyunsaturated fatty acids (PUFA); (g) higher alcohols such as lauryl, cetyl, stearyl, oleyl, behenyl, cholesterol and 2-hexydecanol alcohol; (h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate; (i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils; (j) lipids such as cholesterol, ceramides, sucrose esters and pseudoceramides as described in European Patent Specification No. 556,957; (k) vitamins, minerals, and skin nutrients such as milk, vitamins A, E, and K; vitamin alkyl esters, including vitamin C alkyl esters; magnesium, calcium, copper, zinc and other metallic components; (l) sunscreens such as octyl methoxyl cinnamate (such is sold under the tradename PARSOL MCX) and butyl methoxy benzoylmethane (such is sold under the tradename PARSOL 1789); (m) phospholipids; (n) antiaging compounds such as alpha hydroxy acids, beta hydroxy acids; (o) emollients, moisturizing agents or benefit agents, such as triglyceride oils, mineral oils, petrolatum, and mixtures thereof, more preferably triglycerides such as sunflower seed oil; and (p) mixtures of any of the foregoing components.

Typically the personal care composition also comprises one or more solvents, diluents and adjuvants such as water, ethyl alcohol, isopropyl alcohol or higher alcohols; glycerine, propylene glycol, sorbitol, preservatives, surfactants, fragrances or viscosity adjusters. Such personal care ingredients are commercially available and known to those skilled in the art.

The present invention is illustrated by the following examples which are not to be construed to limit the scope of the invention. Unless otherwise indicated, all parts and percentages are by weight.

Comparative Examples A-N and Examples 1-4

The properties of the cationically modified cellulose ethers are measured as follows:
Nitrogen content, % N: The average weight percent of nitrogen per anhydroglucose repeat unit is determined analytically by using an automated Buchi Kjeldahl distillation unit and titrating with an automated titrimeter.
Number of anhydroglucose repeat units are determined by Gel Permeation Chromatography using multiangle light scattering.
Numbers of moles of ether substituent per mole of anhydroglucose repeat unit are determined by the Morgan modification of the Zeisel method [P. W. Morgan, Ind. Eng. Chem., Anal. Ed., 18, 500 (1946)].
1% viscosity: The solution viscosity is measured at 0.975 weight percent polymer (allowing for 2.5 percent ash, based on polymer weight, and correcting for volatiles), at 25° C. using a #2 spindle at 30 rpm (Brookfield Viscometer).
2% viscosity: The viscosity of a 2 wt.-% aqueous solution at 25° C. is measured using a BROOKFIELD LTV viscometer using spindle No. 4.
The following materials are used in the Examples:
HEC: A hydroxyethyl cellulose having a viscosity of 5,700 cps (mPa·s), measured as a 1 wt.-% aqueous solution at 25° C. using a BROOKFIELD LTV viscometer, about 9,000 to 10,000 anhydroglucose repeat units and an average number of moles of hydroxyethyl groups per mole of anhydroglucose repeat unit, designated as M.S. (hydroxyethyl), of about 2.2;
Q151: A 70 wt.-% aqueous solution of 2,3-epoxypropyltrimethyl ammonium chloride; commercially available from Degussa Corporation as QUAB™ 151;
NaOH: A 25 wt. % aqueous solution of sodium hydroxide;
IPA: anhydrous isopropyl alcohol;
LR 400: a cationically modified hydroxyethyl cellulose having a viscosity of 300-500 cps (mPa·s), measured as a 2 wt.-% aqueous solution, about 1,500 anhydroglucose repeat units and a cationic nitrogen content of 0.8-1.1 percent, based on the total weight of the cellulose ether. The cationically modified hydroxyethyl cellulose is commercially available under the trademark UCARE™ Polymer LR 400.
JR 400: a cationically modified hydroxyethyl cellulose having a viscosity of 300-500 cps (mPa·s), measured as a 2 wt.-% aqueous solution, about 1,500 anhydroglucose repeat units and a cationic nitrogen content of 1.5 to 2.2 percent, based on the total weight of the cellulose ether. The cationically modified hydroxyethyl cellulose is commercially available under the trademark UCARE™ Polymer JR 400.
LR 30M: a cationically modified hydroxyethyl cellulose having a viscosity of 1,250-2,250 cps (mPa·s), measured as a 1 wt.-% aqueous solution, about 4,000 to 7,000 anhydroglucose repeat units and a cationic nitrogen content of 0.8-1.1 percent, based on the total weight of the cellulose ether. The cationically modified hydroxyethyl cellulose is commercially available under the trademark UCARE™ Polymer LR 30M.
JR 30M: a cationically modified hydroxyethyl cellulose having a viscosity of 1,250-2,250 cps (mPa·s), measured as a 1 wt.-% aqueous solution, about 6,000 to 10,000 and a cationic nitrogen content of 1.6 to 1.9 percent, based on the total weight of the cellulose ether. The cationically modified hydroxyethyl cellulose is commercially available under the trademark UCARE™ Polymer JR 30M.

Preparation of Comparative Examples A-G, M, N and Examples 1-4

A reaction vessel equipped with a stirrer, condenser, addition funnels, and nitrogen supply is charged with the amounts of HEC (corrected for ash and volatiles), IPA and distilled water listed in Table 1 below. The reaction vessel is purged with nitrogen for 1 hour. A 25 weight percent aqueous solution of sodium hydroxide is added dropwise over a few minutes at ambient temperature. The slurry is stirred for 20 minutes. The amount of sodium hydroxide, calculated as undiluted product, is listed in Table 1 below. Q151 is added dropwise over a few minutes in an amount listed in Table 1 below. The nitrogen purge is then reduced to a minimum to maintain a positive pressure on the system, and the slurry is heated to 55° C. The slurry is held at 55° C. for 2 hours and is then allowed to cool down. At about 40° C. acetic acid is added dropwise in an amount listed in Table 1 below. After mixing for about 10 minutes, the slurry is filtered. The wet cake is washed twice with 700 g of a IPA/water mixture of a volume ratio of 80:20 (for an 80 gram HEC charge), once with 600 g IPA, and once with IPA containing 2 mL of glyoxal solution (40 volume percent) and 0.4 mL of acetic acid. After the final filtration, the material is dried overnight in a vacuum oven at about 35° C. with a small nitrogen bleed. The product is screened using a 20-mesh sieve screen and oversized particles are ground.

ride, 15 percent sunflower seed oil and 0.5 percent of a cationically modified cellulose ether and water making a total of 100 percent.

For evaluating the sunflower seed oil deposition, the in-vitro skin is treated for 30 seconds with the body wash formulation followed by 15 seconds of rinsing with water at a flow rate of 1 liter/minute having a temperature of 28 to 32° C. The in-vitro skin is allowed to dry in air. The sunflower seed oil deposited on the in-vitro skin is extracted with heptane. The extract is contacted with a solution of 2 molar potassium hydroxide in methanol. The resulting sample is analysed by Gas Chromatography. The sunflower seed oil deposition is measured in ppm (parts per million), based on the weight of the heptane-based extract.

TABLE 2

Sunflower Seed Oil Deposition

| (Comparative) Example | 1% Viscosity | % Nitrogen | SSO* (ppm) |
|---|---|---|---|
| A | 4100 | 0.54 | 2.8 |
| B | 4100 | 0.80 | 15.5 |
| C | 2740 | 0.96 | 18.5 |
| D | 2640 | 1.07 | 25.6 |
| 1 | 3000 | 1.16 | 27.0 |
| 2 | 2340 | 1.22 | 28.3 |
| 3 | 2220 | 1.31 | 26.0 |
| E | 1720 | 1.53 | 18.2 |
| F | 1840 | 1.76 | 13.5 |
| G | 1600 | 2.42 | 7.1 |

TABLE 1

Production and Properties of Cationically Modified Cellulose Ethers

| (Comp.) Example | Grams HEC (active basis) | Grams Q151 (active basis) | Grams IPA | Grams distilled water | Grams NaOH (calc. as undiluted product) | Grams Acetic acid | % Nitrogen | 1% Viscosity* | % Volatiles | % Ash (as NaCl) |
|---|---|---|---|---|---|---|---|---|---|---|
| A | 50.0 | 5.0 | 226 | 47 | 1.77 | 2.7 | 0.54 | 4100 | 2.35 | 0.10 |
| B | 80.0 | 12.7 | 366 | 76 | 2.8 | 4.8 | 0.80 | 4100 | 1.96 | 1.58 |
| C | 50.0 | 9.9 | 226 | 47 | 1.77 | 2.7 | 0.96 | 2740 | 2.33 | 0.32 |
| D | 80.0 | 17.6 | 366 | 76 | 2.8 | 4.8 | 1.07 | 2640 | 2.26 | 1.79 |
| 1 | 80.0 | 19.6 | 366 | 76 | 2.8 | 4.8 | 1.16 | 3000 | 2.60 | 1.19 |
| 2 | 80.0 | 20.2 | 366 | 76 | 2.4 | 4.8 | 1.22 | 2340 | 0.76 | 1.47 |
| 3 | 80.0 | 21.9 | 366 | 76 | 2.4 | 4.8 | 1.31 | 2220 | 1.73 | 1.81 |
| 4 | 80.0 | 24.6 | 366 | 76 | 2.4 | 4.8 | 1.43 | 2160 | 1.67 | 1.74 |
| E | 80.0 | 27.3 | 366 | 76 | 2.4 | 4.8 | 1.53 | 1720 | 2.53 | 1.66 |
| F | 80.0 | 32.3 | 364 | 76 | 2.4 | 4.8 | 1.76 | 1840 | 2.64 | 1.00 |
| G | 77.7 | 47.3 | 376 | 66 | 2.8 | 4.8 | 2.42 | 1600 | 1.14 | 2.59 |
| M | 80.0 | 16.3 | 366 | 76 | 2.55 | 4.8 | 0.92 | 2600 | 1.53 | 1.50 |
| N | 80.0 | 18.6 | 366 | 76 | 2.4 | 4.8 | 1.55 | 2040 | 1.34 | 1.52 |

*The solution viscosity is measured at 0.975 weight percent polymer (allowing for 2.5 percent ash, based on polymer weight, and correcting for volatiles)

Evaluation Method for Sunflower Seed Oil Deposition from Body Wash Formulations

Sunflower seed oil is commonly used as a skin moisturizing agent in body wash formulations. The study on deposition of sunflower seed oil is done on in-vitro skin, commercially available from IMS Inc., CT (USA). Sunflower seed oil is a natural triglyceride with different carbon chain lengths. The oil is derivatized to form methyl esters for Gas Chromatography analysis. Linoleic acid is the major component of sunflower seed oil and used as the indicator. The linoleic acid is measured by GC analysis.

A fixed dimension of in-vitro skin (3 cm×6 cm) is treated with 0.15 gram of a body wash formulation. The body wash formulation comprises 11 percent sodium laurylether sulfate, 4 percent cocamidopropyl betaine, 1.5 percent sodium chlo- TABLE 2-continued Sunflower Seed Oil Deposition

| Comparative Example | 2% Viscosity | % Nitrogen | SSO* (ppm) |
|---|---|---|---|
| I (LR 400) | 300-500 | 0.8-1.1 | 0.8 |
| J (JR 400) | 300-500 | 1.5-2.2 | 1.8 |
| K (LR 30 M) | 1,250-2,250 | 0.8-1.1 | 5.3 |
| L (JR 30 M) | 1,250-2,250 | 1.5-2.2 | 10.9 |

*sunflower seed oil deposition

Table 2 illustrates that personal care compositions of the present invention, such as body wash formulations, exhibit an improved sun flower seed oil deposition.

Evaluation Method for Wet Comb-Ability

The wet combing work (WCW) is measured by using the load cell of an Instron Tensile Tester when a comb is pulled through a wet tress of European single-bleached hair available from International Hair Importers and Products Inc. The wet comb-ability of a shampoo formulation is calculated as follows in terms of the wet combing work done (WCWD), % (percent) reduction of hair tress treated with a shampoo formulation comprising a cellulose ether derivative listed in Comparative Examples D, F, M, N and Examples 2-4 in Table 3 below, as compared to hair tress treated with a control formulation comprising the same ingredients as the shampoo formulation but no cellulose ether, silicone, and ethylene glycol distearate (EGDS).

% WCWD Reduction=[(WCWD$_{control}$−WCWD$_{shampooed}$)]/WCWD$_{control}$]×100 where control means that the hair tress is treated by the control formulation comprising the same ingredients as the shampoo formulation but no cellulose ether, silicone, and EGDS, and shampooed means that the hair tress is treated by the shampoo formulation comprising a cationically modified cellulose ether as listed in Table 3 below. The shampoo formulation comprises a) 0.25 percent of a cationically modified cellulose ether of Comparative Examples D, F, M, N or of Examples 2-4 respectively, b) 1 percent of a polydimethylsiloxane, commercially available from Dow Corning as 1664 Emulsion, c) 15.5% sodium laureth-2-sulfate (SLES), d) 2.6% disodium cocoamphodiacetate (DSCADA), e) 2% ethylene glycol distearate (EGDS), f) 2.2% citric acid (10% aqueous solution), g) 0.4% DMDM Hydantoin (such is sold under the tradename GLYDANT® available from Lonza Inc.), and the remainder being water.

TABLE 3

| (Comparative) Example | 1% Viscosity | % Nitrogen | WCWD Reduction (%) |
|---|---|---|---|
| M | 2600 | 0.92 | 58 |
| D | 2640 | 1.07 | 57 |
| 2 | 2340 | 1.22 | 70 |
| 3 | 2220 | 1.31 | 77 |
| 4 | 2160 | 1.43 | 65 |
| N | 2040 | 1.55 | 48 |
| F | 1840 | 1.76 | 35 |

Table 3 illustrates that personal care compositions of the present invention, such as shampoo formulations, exhibit better conditioning properties, specifically greater reduction in wet combing work after the hair has beend shampooed and then rinsed with water than comparative shampoo formulations comprising cationically modified cellulose ethers which comprise less than 1.15 or more than 1.44 percent of cationic nitrogen, based on the total weight of the cellulose ether.

What is claimed is:

1. A personal care composition comprising:
a water-insoluble active ingredient, and
a cationically modified hydroxyethyl cellulose, wherein
the hydroxyethyl cellulose comprises from 1.5 to 2.5 moles of an hydroxyethyl substituent per mole of anhydroglucose repeat unit, and
the hydroxyethyl cellulose is further substituted with a cationic substituent of the formula I

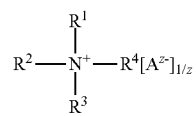

wherein
$R^1$, $R^2$ and $R^3$ each independently are $CH_3$ or $C_2H_5$,
$R^4$ is $CH_2$—CHOH—$CH_2$— or $CH_2CH_2$—,
$A^{z-}$ is an anion, and z is 1, 2 or 3, and
the hydroxyethyl cellulose comprises from 1.15 to 1.44 percent of cationic nitrogen, based on the total weight of the hydroxyethyl cellulose, and
wherein the hydroxyethyl cellulose has 6,000 to 15,000 anhydroglucose repeat units and is not substituted with hydrophobic alkyl or arylalkyl group having 8 to 24 carbon atoms.

2. The personal care composition of claim 1 wherein in the cationic substituent of the formula I $R^1$, $R^2$ and $R^3$ are $CH_3$, $R^4$ is $CH_2$—CHOH—$CH_2$—, $A^{z-}$ is a halide ion and z is 1.

3. The personal care composition of claim 1 wherein the cationically modified hydroxyethyl cellulose comprises from 7,000 to 10,000 anhydroglucose repeat units.

4. The personal care composition of claim 1 in the form of a hair or skin care composition.

5. The personal care composition of claim 1 wherein the water-insoluble active ingredient is a silicone oil, petrolatum or a plant oil.

6. The personal care composition of claim 5 wherein the plant oil is sunflower seed oil or soy bean oil.

7. A personal care composition comprising:
a cationically modified hydroxyethyl cellulose wherein
the hydroxyethyl cellulose comprises from 1.5 to 2.5 moles of a hydroxyethyl substituent per mole of anhydroglucose repean unit, and has 7,000 to 10,000 anhydroglucose repeat units, and
the hydroxyethyl cellulose is further substituted with cationic substituent of formula I

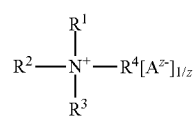

wherein
$R^1$, $R^2$ and $R^3$ each are $CH_3$,
$R^4$ is $CH_2$—CHOH—$CH_2$—,
$A^{z-}$ is a halide, and z is 1, and
the hydroxyethyl cellulose comprises from 1.20 to 1.40 percent of cationic nitrogen, based on the total weight of the hydroxyethyl cellulose, wherein the hydroxyethyl cellulose is not substituted with a hydrophobic alkyl or arylalkyl group having 8 to 24 carbon atoms, and
a water-insoluble active ingredient selected from a silicone oil or a plant oil.

8. The personal care composition of claim 7, wherein the plant oil is sunflower seed oil or soy bean oil.

* * * * *